United States Patent
Chervin et al.

(10) Patent No.: US 7,190,995 B2
(45) Date of Patent: Mar. 13, 2007

(54) SYSTEM AND METHOD FOR ANALYSIS OF RESPIRATORY CYCLE-RELATED EEG CHANGES IN SLEEP-DISORDERED BREATHING

(75) Inventors: Ronald D. Chervin, Ann Arbor, MI (US); Joseph W. Burns, Ann Arbor, MI (US); Nikolas S. Subotic, Ann Arbor, MI (US); Christopher Roussi, Kalamazoo, MI (US)

(73) Assignees: The Regents of the University of Michigan, Ann Arbor, MI (US); Altarum Institute, Ann Arbor, MI (US)

( * ) Notice: Subject to any disclaimer, the term of this patent is extended or adjusted under 35 U.S.C. 154(b) by 401 days.

(21) Appl. No.: 10/866,931

(22) Filed: Jun. 14, 2004

(65) Prior Publication Data

US 2004/0254493 A1 Dec. 16, 2004

Related U.S. Application Data

(60) Provisional application No. 60/478,673, filed on Jun. 13, 2003.

(51) Int. Cl.
*A61B 5/00* (2006.01)
*A61B 5/02* (2006.01)

(52) U.S. Cl. .................. 600/544; 600/534; 600/538

(58) Field of Classification Search .................. None
See application file for complete search history.

(56) References Cited

U.S. PATENT DOCUMENTS

| 6,363,270 | B1 | 3/2002 | Colla et al. |
|---|---|---|---|
| 6,425,861 | B1 | 7/2002 | Haberland et al. |
| 6,529,752 | B2 | 3/2003 | Krausman et al. |
| 6,577,893 | B1 | 6/2003 | Besson et al. |
| 6,641,542 | B2 | 11/2003 | Cho et al. |
| 6,743,167 | B2 | 6/2004 | Balkin et al. |
| 6,993,380 | B1 * | 1/2006 | Modarres ............ 600/544 |

OTHER PUBLICATIONS

F. McNamara et al., Arousal Pattern Following Central and Obstructive Breathing Abnormalities in Infants and Children, *J. App. Physiol.*, 81 (6) : 2651-2657, 1996.

N. Douglas and S. Martin, Arousals and the Sleep Apnea/Hypopnea Syndrome, *Sleep*, 19 (10) : S196-S197, 1996.

C. Guilleminault et al., A Cause of Excessive Daytime Sleepiness: The Upper Airway Resistance Syndrome, *Chest*, vol. 104, p. 781-787, 1993.

I. Ayappa et al., Non-Invasive Detection of Respiratory Effort-Related Arousals (RERAs) by a Nasal Cannula/Pressure Transducer System, *Sleep*, 23 (6) : 763-771, 2000.

(Continued)

*Primary Examiner*—Robert L. Nasser
(74) *Attorney, Agent, or Firm*—Brooks Kushman P.C.

(57) ABSTRACT

A system and method for determining respiratory cycle-related EEG changes (RCREC) for a subject with sleep-disordered breathing are provided. The method includes receiving an EEG signal from the subject using at least one sensor, and defining at least two respiratory cycle segments within each respiratory cycle. The method further includes determining an EEG power of the EEG signal during each of the at least two respiratory cycle segments, and determining RCREC by calculating a difference between a maximum EEG segment power and a minimum EEG segment power.

40 Claims, 4 Drawing Sheets

OTHER PUBLICATIONS

D. Navajas et al., Assessment of Airflow Obstruction During CPAP by Means of Forced Oscillation in Patients with Sleep Apnea, *Am J Respir Crit Care Med*, vol. 157, pp. 1526-1530, 1998.

J. Black et al., Upper Airway Resistance Syndrome: Central Electroencephalographic Power and Changes in Breathing Effort, *Am J Respir Crit Care Med*, vol. 162, pp. 406-411, 2000.

K. Dingli et al., Electroencephalographic Spectral Analysis: Detection of Cortical Activity Changes in Sleep Apnoea Patients, *Eur Respir J*, 20: 1246-1253, 2002.

L. Bennett et al., Sleep Fragmentation Indices as Predictors of Daytime Sleepiness and nCPAP Response in Obstructive Sleep Apnea, *Am J Respir Crit Care Med*, vol. 158, pp. 778-786, 1998.

J. Stradling et al., Prevalence of Sleepiness and its Relation to Autonomic Evidence of Arousals and Increased Inspiratory Effort in a Community Based Population of Men and Women, *J. Sleep Res.*, 9: 381-388, 2000.

M. Ferrara et al., Regional Differences of the Temporal EEG Dynamics During the First 30 Min of Human Sleep, *Neuroscience Research*, 44: 83-89, 2002.

H. Moldofsky et al., Musculoskeletal Symptoms and Non-REM Sleep Disturbance in Patients with "Fibrositis Syndrome" and Healthy Subjects, *Psychosomatic Medicine*, 37 (4) : 341-351, 1975.

D. Dijk et al., Time Course of EEG Power Density During Long Sleep in Humans, *Am J Physiol*, 258: R650-R661, 1990.

K. Rees et al., Arousal Responses from Apneic Events During Non-Rapid-Eye-Movement Sleep, *Am J Respir Crit Care Med*, vol. 152, pp. 1016-1021, 1995.

E. Svanborg and C. Guilleminault, EEG Frequency Changes During Sleep Apneas, *Sleep*, 19(3) : 248-254, 1996.

H. Bandla and D. Gozal, Dynamic Changes in EEG Spectra During Obstructive Apnea in Children, *Pediatric Pulmonology*, 29: 359-365, 2000.

D. Pitson and J. Stradling, Autonomic Markers of Arousal During Sleep in Patients Undergoing Investigation for Obstructive Sleep Apnoea, Their Relationship to EEG Arousals, Respiratory Events and Subjective Sleepiness, *J Sleep Res*, 7: 53-59, 1998.

R. Davies et al., What is an Arousal and How Should it be Quantified?, *Sleep Medicine Reviews*, 1(2) : 87-95, 1997.

D. Chugh et al., Neurobehavioral Consequences of Arousals, *Sleep*, 19(10) : S198-S201, 1996.

S. Martin et al., The Effect of Sleep Fragmentation on Daytime Function, *Am J Respir Crit Care Med*, vol. 153, pp. 1328-1332, 1996.

R. Heinzer et al., Slow-Wave Activity in Sleep Apnea Patients Before and After Continuous Positive Airway Pressure Treatment: Contribution to Daytime Sleepiness, *Chest*, 119(6) : 1807-1813, 2001.

D. Poyares et al., Arousal, EEG Spectral Power and Pulse Transit Time in UARS and Mild OSAS Subjects, *Clinical Neurophysiology*, 113: 1598-1606, 2002.

J. Stradling et al., Variation in the Arousal Pattern after Obstructive Events in Obstructive Sleep Apnea, *Am J Respir Crit Care Med*, vol. 159, pp. 130-136, 1999.

D. Dijk and D. Beersma, Effects of SWS Deprivation on Subsequent EEG Power Density and Spontantous Sleep Duration, *Electroencephalography and Clinical Neurophysiology*, 72: 312-320, 1989.

A. Borbely, A Two Process Model of Sleep Regulation, *Human Neurobiology*, 1: 195-204, 1982.

C. Guilleminault et al., Sleep and Daytime Sleepiness in Upper Airway Resistance Syndrome Compared to Obstructive Sleep Apnoea Syndrome, *Eur Respir J*, 17: 838-847, 2001.

F. Morisson et al., Spectral Analysis of Wakefulness and REM Sleep EEG in Patients with Sleep Apnoea Syndrome, *Eur Respir J*, 11: 1135-1140, 1998.

D. Dijk et al., Dynamics of Electroencephalographic Sleep Spindles and Slow Wave Activity in Men: Effect of Sleep Deprivation, *Brain Research*, 626: 190-199, 1993.

S. Uchida et al., Sigma (12-15 Hz) and Delta (0.3-3 Hz) EEG Oscillate Reciprocally Within NREM Sleep, *Brain Research Bulletin*, vol. 27, pp. 93-96, 1991.

B. Ondze et al., Sleep Architecture, Slow Wave Activity and Sleep Spindles in Mild Sleep Disordered Breathing, *Clinical Neurophysiology*, 114: 867-874, 2003.

F. Morisson et al., Daytime Sleepiness and EEG Spectral Analysis in Apneic Patients Before and After Treatment with Continuous Positive Airway Pressure, *Chest*, 119(1) : 45-52, 2001.

J. Gora et al., Evidence of a Sleep-Specific Blunted Cortical Response to Inspiratory Occlusions in Mild Obstructive Sleep Apnea Syndrome, *Am J Respir Crit Care Med*, vol. 166, pp. 1225-1234, 2002.

\* cited by examiner

SYSTEM AND METHOD FOR ANALYSIS OF RESPIRATORY CYCLE-RELATED EEG CHANGES IN SLEEP-DISORDERED BREATHING

CROSS-REFERENCE TO RELATED APPLICATIONS

This application claims the benefit of U.S. provisional application Ser. No. 60/478,673 filed Jun. 13, 2003, which is incorporated by reference herein.

STATEMENT REGARDING FEDERALLY SPONSORED RESEARCH OR DEVELOPMENT

The invention was made in part with Government support under Grant No. R01 HD38461 from NIH/NICHD, NHLBI and Grant No. K02 NS02009 from NIH/NINDS. The Government has certain rights to the invention.

BACKGROUND OF THE INVENTION

1. Field of the Invention

The present invention relates to a system and method for the analysis of respiratory-cycle related electroencephalogram (EEG) changes in sleep-disordered breathing.

2. Background Art

Obstructive sleep-disordered breathing (SDB) in children includes obstructive sleep apnea, upper airway resistance syndrome, and obstructive hypoventilation. In obstructive sleep apnea, repeated airflow cessation (apnea) or decrement (hypopnea) leads to arousal, oxygen desaturation, and sleep fragmentation. In upper airway resistance syndrome, repeated partial closure of the upper airway leads to sequences of increasing effort to breathe, terminated by brief arousals in the absence of significant hypoxemia. In obstructive hypoventilation, a narrowed airway leads to steady but increased effort to breathe and hypercarbia, without visible arousals. The most frequent cause of SDB in children is adenotonsillar hypertrophy, and adenotonsillectomy in these children is thought to be a highly effective intervention. Causes in adults may include obesity, genetic contributions, and neurophysiological factors.

Several studies suggest that the prevalence of obstructive sleep apnea among children is 1 to 3%, whereas the prevalence of habitual snoring, with or without obstructive SDB, is 5 to 12%. The prevalence of upper airway resistance syndrome and obstructive hypoventilation are unknown, but these disorders could be present in a substantial portion of children with habitual snoring. Severe childhood SDB can lead to failure to thrive, growth retardation, cor pulmonale, and systemic hypertension. Unrecognized or incompletely treated SDB may contribute to behavioral and cognitive problems, including inattentive and hyperactive behavior, aggressive conduct, and daytime sleepiness.

As childhood SDB is common and treatable, identification of the condition is important, preferably before consequences develop. However, most children with SDB may not be identified. Epidemiological data from adults show that >90% of women and >80% of men with obstructive sleep apnea are not diagnosed. Among children, SDB was undiagnosed in 92% of affected children who participated in one community-based research study.

Unfortunately, the mechanism by which sleepiness and other cognitive changes are produced in SDB is not fully understood, and the optimal approach to the identification of children with SDB is controversial. Most attention has been focused on the role of arousals, which typically occur at the termination of each apnea, hypopnea, or transient period of increased respiratory effort. Arousals from sleep are believed to contribute substantially to SDB morbidity, and cortical EEG signals obtained via polysomnography have been used to define sleep and wakefulness for many years. In the assessment of patients for SDB, current state-of-the-art methodology focuses largely on the apnea/hypopnea index: the number of times per hour of sleep that a patient has absence of breathing (apnea), diminished breathing (hypopnea), or difficult breathing (respiratory event-related arousal).

To determine the apnea/hypopnea index, patients undergo polysomnographic recordings wherein technicians manually classify sleep stages and manually count episodes of apneas, hypopneas, and sometimes the more subtle respiratory event-related arousals. Manual scoring of apneic events recorded on sleep studies is time-consuming, expensive, subject to inter-scorer variability, and based on definitions that can vary considerably between laboratories. Software that automates the process has been available for years, but generally is not considered to be an adequate substitute. The main result of manual apnea scoring—the rate of events per hour of sleep—only poorly predicts sleepiness, inattention, hyperactivity, and outcomes of sleep-disordered breathing in children and adults. For example, randomized controlled trials confirm that SDB causes excessive daytime sleepiness, but the rate of apneas and hypopneas—often used as the best single polysomnographic measure of SDB severity—only predicts about 11% of the variance in objectively measured sleepiness.

One possible explanation is that subtle but clinically-relevant SDB is often missed, as features of SDB that most affect outcomes may not be recorded or analyzed. In particular, many patients, and especially children, do not always show visually-recognizable EEG arousals after apneic events (see McNamara et al., *J Appl Physiol* 1996, 81:2651–7). In practice, arousals are most often defined primarily by transient increases in EEG frequency. More subtle arousals, as reflected by autonomic changes in the absence of visible cortical EEG activation, can also cause sleepiness when experimentally induced (see Douglas and Martin, *Sleep* 1996, 19:S196–7), but may not correlate any better with sleepiness in non-experimental settings. Computerized approaches to this problem have focused entirely on apneic events that appear themselves to be inadequate predictors of outcomes.

Clearly, associations between apnea/hypopnea indices and subjective sleepiness can be difficult to detect. In the largest samples, subjects with the most frequent apneic events, in comparison to those with the least, score only 2 points higher on a 24-point subjective sleepiness scale. In addition, snoring predicts sleepiness even after accounting for the rate of apneas and hypopneas. Among children, surveys about snoring and other clinical signs of SDB repeatedly show robust correlations with behavioral morbidity, but data from polysomnographic studies of SDB show less consistent associations. These findings parallel those from adults, among whom polysomnographic measures tend to explain only small portions of measured sleepiness, and a history of snoring still predicts sleepiness after objective measures are taken into account.

A desire to improve the ability of polysomnograms to predict SDB outcomes has given rise to new equipment and strategies to monitor breathing or breathing effort, such as esophageal pressure monitoring (see Guilleminault et al., *Chest* 1993, 104:781–7), nasal pressure monitoring (see Ayappa et al., *Sleep* 2000, 23:763–71), and the forced oscillation technique (see Navajas et al., *Am J Resp Crit Care Med* 1998, 157:1526–30). Other approaches have focused on non-visible EEG changes detected by signal analysis (see Black et al., *Am J Crit Care Med* 2000, 162:406–11; Bandla and Gozal, *Pediatr Pulmonol* 2000, 29:359–65; Dingli et al., *Eur Respir J* 2002, 20:1246–53), body movements (see Bennett et al., *Am J Resp Crit Care Med* 1998, 158:778–86), or subtle autonomic changes (see Pitson and Stradling, *J Sleep Res* 1998, 7:53–9; Stradling et al., *J Sleep Res* 2000, 9:381–8). However, none of these methods, all linked to the concept that discrete apneic events in some way cause sleepiness, have substantially improved prediction of important SDB outcomes.

Therefore, physiologically important features of SDB or sleepiness may not be adequately assessed by current methods. The problem may be particularly relevant to children, whose apneic events can be short, subtle, unaccompanied by visible arousal, and difficult to detect.

SUMMARY OF THE INVENTION

Accordingly, a method for determining respiratory cycle-related EEG changes (RCREC) for a subject is provided. The method includes receiving an EEG signal from the subject using at least one EEG sensor, and defining at least two respiratory cycle segments within each respiratory cycle. The method further includes determining an EEG power of the EEG signal during each of the defined respiratory cycle segments, and determining RCREC by calculating a difference between a maximum EEG segment power and a minimum EEG segment power.

In accordance with the present invention, determining an EEG power can include digitally filtering the EEG signal with any of a large variety of filters, such as a $5^{th}$ order Butterworth filter. Alternatively, determining the EEG power can include taking a short-time Fourier transform of the EEG signal. The EEG power is determined for one or more frequencies, which can be within frequency ranges such as delta (approximately 1–4 Hz), theta (approximately 5–7 Hz), alpha (approximately 8–12 Hz), sigma (approximately 13–15 Hz), or beta (approximately 16–30 Hz).

The method of the present invention can further include normalizing the EEG power for each respiratory cycle segment by a mean EEG power during the entire respiratory cycle, and averaging the EEG segment powers over a plurality of respiratory cycles. In one approach, the EEG signal is recorded over about the first three hours of nocturnal sleep, but shorter or longer time periods can also be utilized.

According to the present invention, the method can further include receiving a respiratory signal from the subject. The respiratory signal can include, for example, at least one of a nasal airflow and an oral airflow, at least one of a chest excursion and an abdominal excursion, an intrathoracic pressure, or respiratory muscle activity. Typically, the respiratory cycle is divided into four fixed time segments defined by maxima, minima, and midpoints of inspiratory and expiratory phases of the respiratory cycle.

The method according to the present invention can further include amplifying the EEG signal, converting the EEG signal from analog to digital format, storing EEG data in memory, and displaying EEG data on a display. Still further, the method can include comparing values of RCREC before and after intervention to treat sleep-disordered breathing, and comparing RCREC values with values of a sleepiness measure, cognitive function, behavior, psychiatric pathology, IQ, or other aspects of health and quality of life.

Correspondingly, a system is provided for determining respiratory cycle-related EEG changes (RCREC) in a subject. The system includes at least one EEG sensor arranged to obtain an EEG signal from the subject, and a respiratory measurement device for defining at least two segments of each respiratory cycle. A processor in communication with the at least one sensor and the respiratory measurement device determines an EEG power of the EEG signal during each of the at least two respiratory cycle segments, and determines RCREC by calculating a difference between a maximum EEG segment power and a minimum EEG segment power.

In one approach, the processor utilizes digital filtering, such as with at least one $5^{th}$ order Butterworth filter, of the EEG signal to determine the EEG power. In another approach, the processor utilizes a short-time Fourier transform of the EEG signal to determine the EEG power. The processor determines the EEG power for one or more frequencies within at least one frequency range, such as delta (approximately 1–4 Hz), theta (approximately 5–7 Hz), alpha (approximately 8–12 Hz), sigma (approximately 13–15 Hz), or beta (approximately 16–30 Hz). Preferably, the processor normalizes the EEG power for each respiratory cycle segment by a mean EEG power during the entire respiratory cycle, and averages the EEG segment powers over a plurality of respiratory cycles.

The respiratory measurement device receives a respiratory signal from the subject and can include, for example, at least one airflow sensor for measuring at least one of a nasal airflow and an oral airflow, at least one position sensor for measuring at least one of a chest excursion and an abdominal excursion, at least one pressure sensor for measuring intrathoracic pressure, or at least one EMG sensor for measuring respiratory muscle activity. The system can further include an amplifier in communication with the at least one sensor for amplifying the EEG signal, and an A/D converter in communication with the processor for converting the EEG signal from analog to digital format. Still further, the system can include memory in communication with the processor for storing EEG data, and a display in communication with the processor for displaying EEG data.

In further accordance with the present invention, a computer readable medium for determining respiratory cycle-related EEG changes (RCREC) in a subject is provided. The medium includes computer readable instructions for determining an EEG power of a received EEG signal for a plurality of respiratory cycle segments, and determining RCREC by calculating a difference between a maximum mean EEG segment power and a minimum mean EEG segment power. In one approach, the medium can also include computer readable instructions for normalizing the EEG power for each respiratory cycle segment by a mean EEG power during the entire respiratory cycle, and for averaging the normalized EEG segment powers over a plurality of respiratory cycles.

The above features and advantages along with other features and advantages of the present invention are readily apparent from the following detailed description of the best mode for carrying out the invention when taken in connection with the accompanying drawings.

DETAILED DESCRIPTION OF THE PREFERRED EMBODIMENT(S)

The present invention is a system and method for assessment of SDB which correlates EEG changes with the respiratory cycle to produce a clinically useful measure of the extent to which difficulty breathing during sleep may affect brain function, sleepiness, behavior, cognition, or other processes affected by SDB. The system and method of the present invention recognize that brief, non-visible changes in cortical activity ("microarousals") may occur on a breath-to-breath basis, between the discrete events that define apneas, hypopneas, or respiratory event-related arousals during the sleep of patients with SDB. These microarousals produce respiratory-cycle-related decrements in low-frequency EEG power and contribute to excessive daytime sleepiness and other neurobehavioral, cognitive, or health-related consequences of SDB. Most children with SDB spend only a small proportion of their sleep in apnea, but many non-apneic breaths still show high upper airway resistance. Airway resistance or snoring with inspiration could promote thousands of brief, non-visible arousals and impair the restorative function of sleep.

The present invention utilizes a new EEG signal analysis method that identifies non-visible EEG changes during individual respiratory cycles through a new measure, called respiratory cycle-related EEG changes (RCREC). RCREC is defined as the proportion of EEG power, at a specific frequency or within specific frequency bands, that can be explained as a function of respiratory cycle timing. Averaging of EEG activity during distinct portions of many respiratory cycles is utilized as a way to define subtle respiratory-cycle-dependent EEG changes, and EEG activity during a specific segment of a breathing cycle is preferably standardized to the level of activity occurring during the entire cycle. The system and method of the present invention use specific EEG frequency components to better identify the disruption of deep non-REM sleep on a breath-to-breath basis.

As described in more detail below, the system and method of the present invention predict sleepiness and other outcomes better than do currently available techniques. Validity of the system and method of the present invention is supported by previous observations that snoring, independent of measured apnea, still predicts sleepiness. This suggests that the large number of breathing cycles that occur between the minority obviously affected by apneas and hypopneas may contribute to sleepiness, and perhaps other outcomes. Additional experience from sleep labs shows that the effort to breathe is increased in sleep apneics during otherwise normal-appearing breaths that occur between apneas and hypopneas. Therefore, increased respiratory effort on a breath-to-breath basis may arouse the brain, and affect recorded brain waves, in a manner not appreciable by the human eye but readily detectable by the computerized analysis of the present invention.

Figure 1:
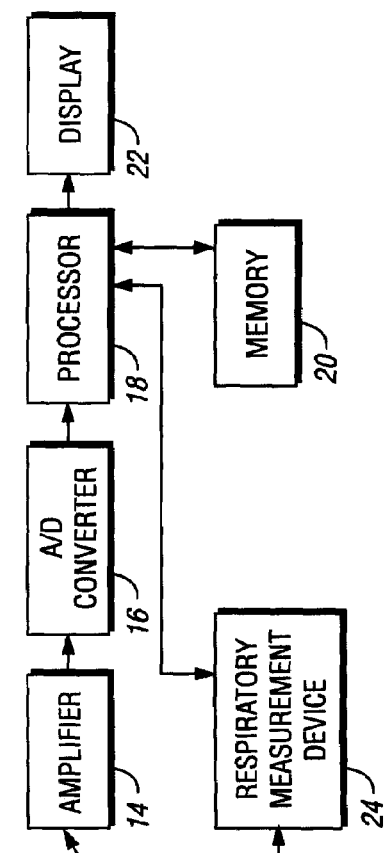
FIG. 1 is a schematic diagram of a thermocouple-derived oral/nasal airflow signal, wherein respiratory cycle segments are defined by maxima, minima, and mid-points of the inspiratory and expiratory phases.
Figure 2:
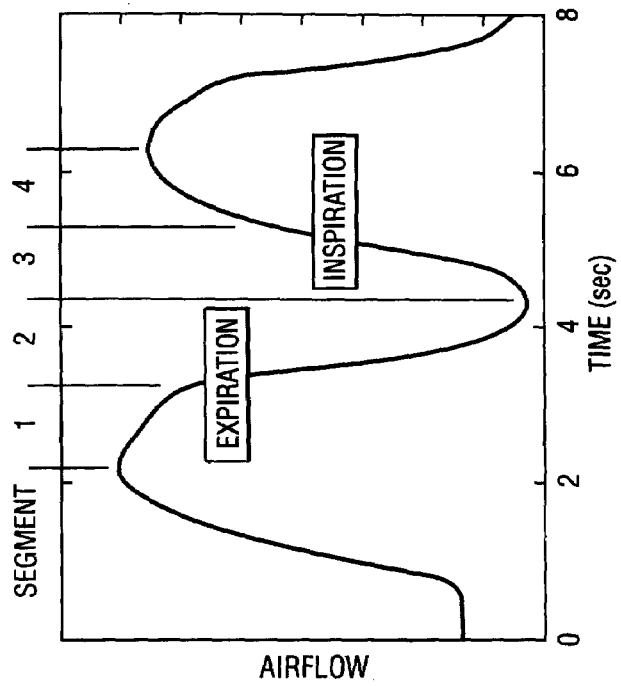
FIG. 2 is a block diagram of a system utilized in determining the respiratory cycle-related EEG changes (RCREC) in accordance with the present invention.
Figure 2:

Turning first to FIGS. 1 and 2, a respiratory measurement device 24 can be used to obtain a respiratory signal from a subject and, in conjunction with a processor 18, define the maxima and minima of the inspiratory and expiratory phases for each respiratory cycle (breath cycle), where midpoints are identified between the defined maxima and minima. In one approach, the respiratory measurement device 24 is an airflow sensor, such as a thermocouple, which measures oral and/or nasal airflow. Other respiratory measurement devices contemplated by the present invention include position sensors for measuring chest or abdominal movement, EMG sensors for measuring respiratory muscle activity, pressure sensors for measuring intrathoracic pressure, or the like. The resulting 5 points create 4 fixed time segments as shown in FIG. 1. For occasional clipped portions of respiratory cycles, midpoints of flat regions are preferably used to approximate locations of maxima and minima. Of course, more or fewer than 4 time segments can be utilized in accordance with the present invention. The corresponding frequency-specified EEG power in each respiratory cycle segment can then be determined as explained below.

To determine RCREC according to the present invention, data can be analyzed from the whole night, all sleep during the night, or specific sleep stages. The first 3 hours of nocturnal sleep are preferably utilized for three reasons. First, cortical slow wave activity, thought to be critical to the restorative function of sleep, is most prominent during this time. Second, in severe adult apneics, slow wave activity in the first nocturnal sleep cycle is deficient, to an extent correlated with daytime sleepiness, but increases after the apnea is treated. Third, in comparisons of analyses of entire night data to those that focused on the first 3 hours, the former did not prove more effective. The method of the present invention excludes apneas and unusual breaths, and divides each remaining respiratory cycle into 4 segments as shown in FIG. 1.

With reference to FIG. 2, a system 10 for determining RCREC according to the present invention is illustrated. Digital EEG data obtained via polysomnography for adults and children typically includes two to sixteen EEG electrodes 12 or sensors (e.g., F3-A2, F4-A1, C3-2, C4-A1, O1-A2, O2-A1 of the 10–20 international electrode placement system). Other variables, typically 2 electro-oculogram channels (right and left outer canthi), chin and bilateral anterior tibialis surface EMG, 2 EKG leads, nasal and oral airflow (thermocouples), nasal pressure through pediatric sensor cannulae (e.g., Pro-Tech, Woodinville, Wash.), thoracic and abdominal excursion (piezoelectric strain gauges), finger oximetry ($SaO_2$ and oximetry "pulse wave"; e.g., Ohmeda 3740, Louisville, Co.), and esophageal pressure (water filled catheter: 6-French pediatric feeding tube) can be simultaneously recorded.

As is known in the art, during polysomnography a continuous stream of voltage data representative of an EEG signal is detected by the electrodes 12 affixed to the subject's scalp, and the EEG signal is sampled and digitized. Specifically, an amplifier 14 in communication with electrodes 12 is used to amplify the EEG signal, after which the amplified signal is sent to an A/D converter 14 that converts the signal from analog to digital format. The EEG signal can also undergo additional pre-processing for removing artifacts due to data collection and physiological causes (e.g., sorting to remove extremely short or long respiratory cycle lengths). The digital EEG signal and the respiratory signal are sent to a processor 18 which processes the signals as described in detail below, typically stores EEG data in memory 20, and can display EEG data on a display 22. Preferably, recordings are made on digital equipment such as Telefactor DEEG/TWIN (W. Conshohocken, Pa.), and components other than those described above can be alternatively utilized in accordance with the present invention.

Figure 3:
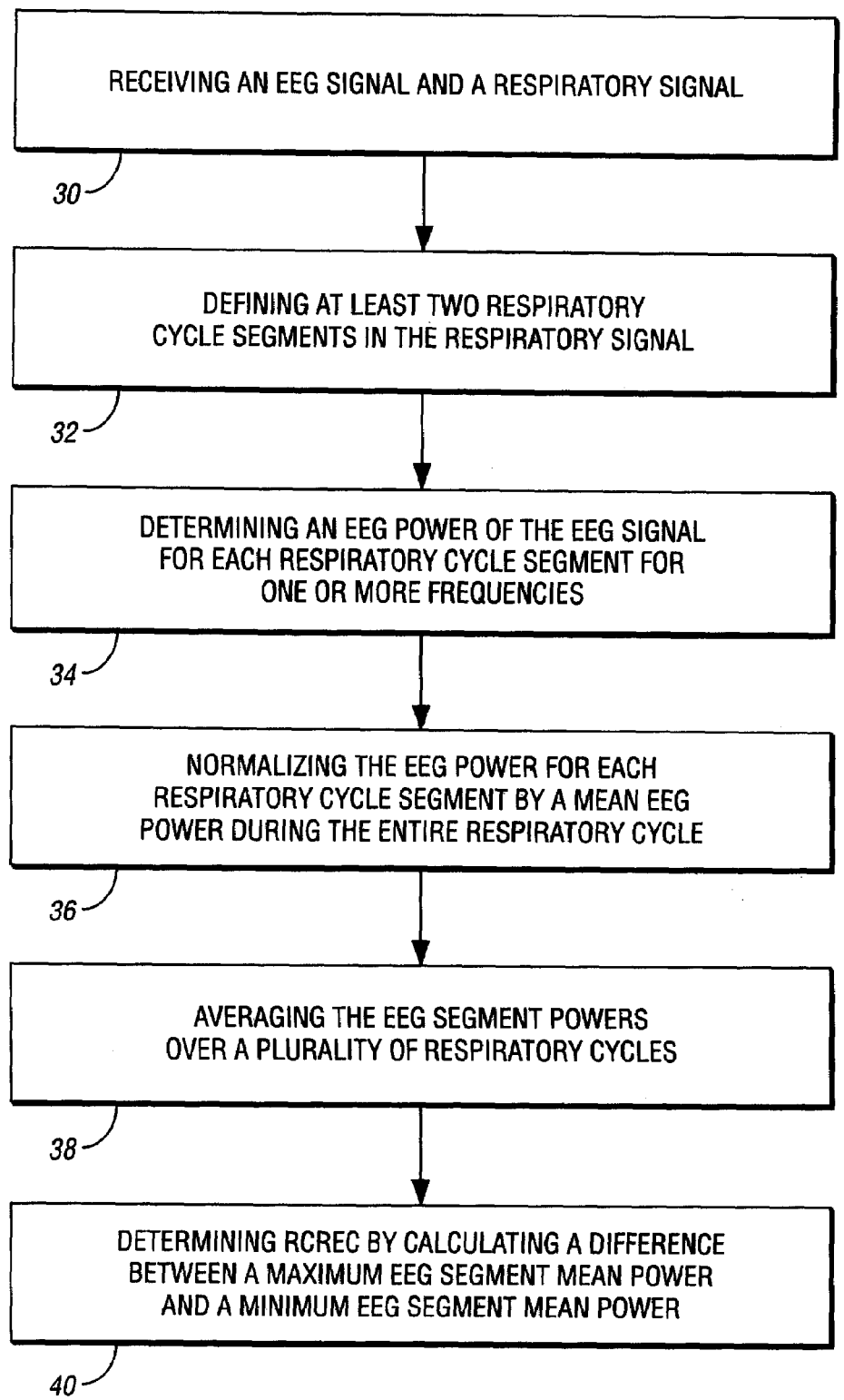
FIG. 3 is a flow chart outlining a method for determining RCREC in accordance with the present invention.

Turning now to FIG. 3, a flow diagram illustrating the method of determining RCREC according to the present invention is shown. The method includes receiving an EEG signal and a respiratory signal (block 30), defining at least two respiratory cycle segments in the respiratory signal (block 32), determining an EEG power of the EEG signal of each respiratory cycle segments for one or more frequencies (block 34), normalizing the EEG power for each respiratory cycle segment by a mean EEG power during the entire respiratory cycle (block 36), averaging the normalized segment EEG powers over a plurality of respiratory cycles (block 38), and determining RCREC by calculating a difference between a maximum EEG segment mean power and a minimum EEG segment mean power (block 40).

In one approach, conditioning of the EEG signal is accomplished through zero-phase digital filtering of the EEG signal received from at least one EEG electrode 12 (typically C3-A2). Digital filtering is used to determine the EEG power for each respiratory cycle segment for one or more frequencies, preferably within at least one of the delta (approximately 1–4 Hz), theta (approximately 5–7 Hz), alpha (approximately 8–12 Hz), sigma (approximately. 13–15 Hz), and beta (approximately 16–30 Hz) frequency ranges. The EEG power measures the amplitude, regularity, and frequency of brain waves at the specified frequency or within specified EEG frequency ranges. All ranges relevant to sleep staging are preferably included in the method of the present invention because cortical arousal could manifest either as reduction in slow wave activity or appearance of faster rhythms. Of course, frequency ranges other than those described herein could also be measured in accordance with the present invention.

Figure 4:
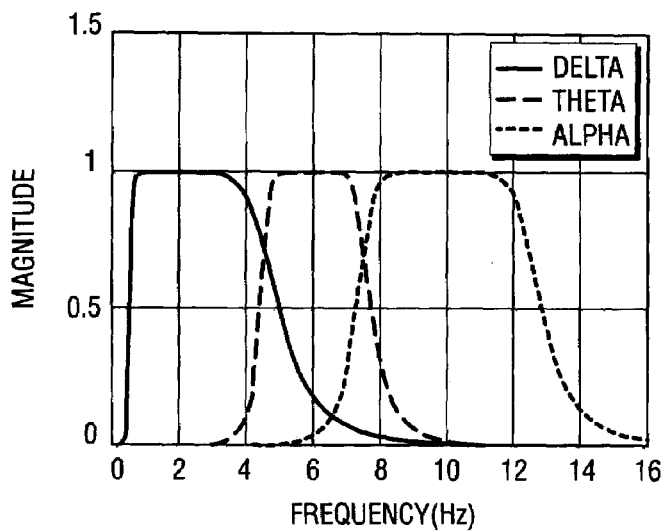
FIG. 4 is a graph of the magnitude of the frequency domain impulse response functions of the digital filters utilized for signal conditioning in one approach according to the present invention.

For example, $5^{th}$ order Butterworth filters can be used to determine the EEG power in the delta, theta, and alpha frequency ranges, wherein the frequency domain impulse response function of the filters in each frequency range are shown in FIG. 4. Of course, this filter selection is merely exemplary, and any filter arrangement capable of measuring EEG power within the desired frequency ranges can be utilized according to the present invention. The parameters of the digital filters are chosen to preferably provide a maximally-flat response over the filter passband, and a response falloff at the passband edges that is sufficiently fast to minimize the effects of spectral leakage, particularly at very low frequencies.

Figure 5A:
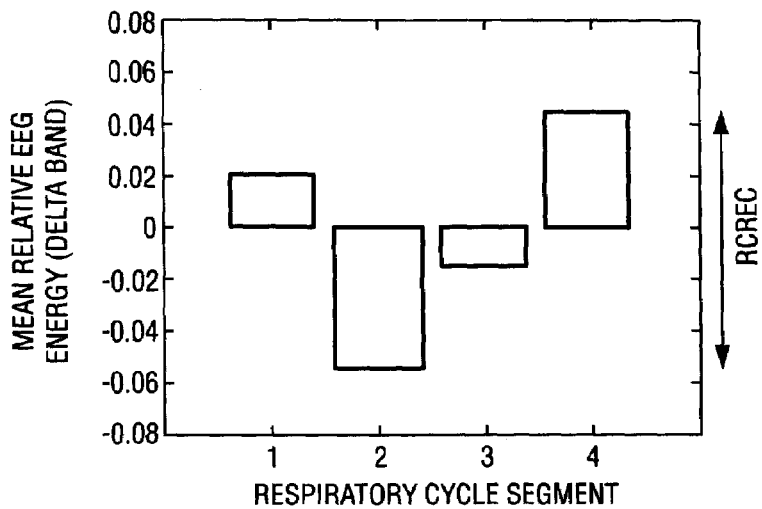
FIGS. 5A and 5B are graphs of mean relative delta-frequency EEG power as a function of respiratory cycle segment for a subject before and after adenotonsillectomy to treat SDB, respectively, wherein RCREC is defined as the difference between the maximum and minimum EEG power across the respiratory cycle.
Figure 5B:
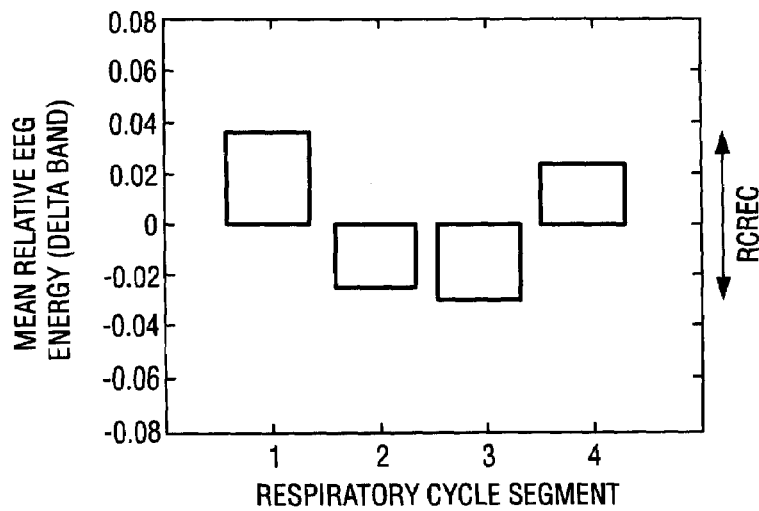

The EEG power is then assessed for the specified frequency or frequency ranges during the time region defined by each respiratory cycle segment, wherein the respiratory cycle segment information is determined by processor 18 through communication with respiratory measurement device 24. The EEG power during each segment is preferably normalized with respect to the mean power during the entire respiratory cycle. This most likely eliminates considerable noise, as changes in sleep stages on a longer time frame could possibly overwhelm and obscure small changes associated with short portions of the respiratory cycle. More particularly, the frequency-specific EEG power in any given respiratory cycle segment is standardized by expression as a proportion (mean power for the segment divided by mean power for the entire cycle) minus 1.00. Thus, if no difference in EEG power occurs across the respiratory cycle, all segments have a mean relative power of 0.00. Mathematically, for a specific frequency or frequency range, computation of the ratio of EEG power during the respiratory cycle segment to total power during the entire respiratory cycle ($c_i$) is accomplished by the following formula:

$$c_i = \frac{\int_{T_i} |S(t)|^2 dt}{\int_T |S(t)|^2 dt} - 1$$

where S is the filtered EEG signal for a specific frequency or over a specific frequency range as determined by digital filtering, T is respiratory cycle-defined time region, and $T_i$ is the segment-defined time region. The proportions specific to each segment are then preferably averaged over many respiratory cycles (preferably about 2500), allowing averaging of the subsequent cortical activity, cancellation of "noise," and emergence of the evoked potentials of interest. The mean powers for the 4 respiratory cycle segments are compared and can be tested for significant differences using ANOVA or the like. The magnitude of RCREC for a given polysomnogram is calculated as the maximum difference between mean segment powers (the difference between the highest mean segment-specific EEG power and the lowest) for a particular frequency or frequency range as shown in FIG. 5.

In an alternative approach, short-time Fourier transform (STFT) is used to compute the EEG power for each respiratory cycle segment for a desired frequency or frequency range. To determine RCREC, a time-evolved representation of the EEG power spectrum $S(f_o, t)$ is generated for each respiratory cycle segment, and a time-frequency decomposition of the EEG is made using the STFT. The STFT takes the Fourier transform of a time series subset defined by a sliding window. The EEG power is then assessed for a specific frequency or range of frequencies during time segments defined by each respiratory cycle (FIG. 1). The EEG power for each frequency or frequency range is summed over respiratory cycle segments. The mean EEG power during each segment is normalized with respect to the mean power during the entire respiratory cycle. Mathematically, for a specific frequency or frequency range, computation of the ratio of EEG power during the respiratory cycle segment to total power during the entire respiratory cycle ($c_i$) is accomplished by the formula:

$$c_i = \frac{\frac{1}{T_i}\int_F\int_{T_i}|S(f,t)|^2 df dt}{\frac{1}{T}\int_F\int_T |S(f,t)|^2 df dt} - 1$$

where S is STFT of EEG data, F is the frequency or frequency band, T is the respiratory cycle-defined time region, and $T_i$ is the segment-defined time region.

Although digital filtering and short-term Fourier transforms have been described herein for determination of RCREC, many alternative mathematical approaches, such as wavelet theory, could also be used to identify relative changes in EEG signals during specified segments of respiratory cycles. Furthermore, different EEG electrodes could be utilized. For example, delta energy EEG waves are produced predominantly near the front of the head, and recordings from frontal cortex sites might therefore be expected to enhance RCREC that is based on delta energy. Similarly, measures of breathing might be used that could be smoother or more accurate than the thermocouple signals used herein. Also, alternative signal processing approaches, such as entropy measures or detection formalisms, are available to quantify the EEG relationship to breathing in addition to RCREC.

Regardless of the specific technique used to obtain RCREC, the system and method according to the present invention will preferably identify EEG power associated with specified portions of the respiratory cycle, focus on one or more physiologically-meaningful EEG frequency ranges, average results over many respiratory cycles, and control results during any one respiratory cycle segment for background EEG patterns present during that entire respiratory cycle.

As will be appreciated by one of skill in the art, the present invention may be embodied as a method, a data processing system, or a computer program product. Accordingly, the present invention may take the form of an entirely hardware embodiment, an entirely software embodiment, or an embodiment combining hardware and software aspects. Electronic hardware can be either dedicated equipment or equipment internal to a computer, and software can be embodied in computer readable material for use by computers or software resident in memory or a programmed chip for use in computers or dedicated equipment. A computer program product according to the present invention can be in the form of a computer-usable storage medium having computer-usable program code embodied in the medium. Any suitable computer readable medium may be utilized including hard disks, CD-ROMs, optical storage devices, magnetic storage devices, or the like.

It is also understood that each block of the flow chart illustrated in FIG. 3 can be implemented by computer program instructions. Instructions execute via the processor of a computer, and these computer program instructions can be stored in a computer readable memory or loaded onto a computer.

The potential physiological meaning and clinical performance of RCREC were initially tested among 10 subjects 6 to 10 years of age. Nine subjects were scheduled for adenotonsillectomy and one for hernia repair (control), where 5 subjects had SDB by standard measures and 5 did not. Before the scheduled surgery and again one year later, each subject underwent laboratory-based polysomnography.

All scoring of subject records was performed in blinded fashion by one technician, and sleep stage scoring followed standard protocols. Apneas were scored when airflow was absent for at least 2 breath cycles, and hypopneas were scored when at least 2 breath cycles of diminished airflow, chest movement, or abdominal movement were followed by an arousal, an awakening, or a 4% oxygen desaturation. During the day that followed polysomnography, a Multiple Sleep Latency Test (MSLT) and neuropsychological battery were administered (see Carskadon et al., *Sleep* 1986, 9:519–24). Sleep onset for each nap was scored at the first epoch of stage 1 sleep, and nap attempts that contained no sleep were assigned a latency of 20 minutes: Cognitive testing included one objective measure of attention, the Integrated Visual and Auditory (IVA™) Continuous Performance Test (auditory portion).

The first 360 thirty-second epochs (3 hours) of scored sleep in each polysomnogram were analyzed and RCREC was calculated according to the STFT approach of the present invention described above. Respiratory cycles that were below the $5^{th}$ percentile or above the $95^{th}$ percentile for amplitude or length were rejected to avoid inclusion of apneas or spurious deviations in a typically sinusoidal airflow pattern. RCREC was then compared between the subjects, and before and after surgery. Relationships between RCREC and 3 other variables were explored with the nonparametric Spearman correlation coefficient rho. The 3 variables were rates of apneas and hypopneas, sleepiness as defined by mean sleep latency on a MSLT, and inattention as defined by IVA auditory omission scores.

In pre-operative polysomnograms of all subjects except the one control and one child without SDB, the spectral power of one or more specific frequency bands differed significantly between respiratory cycle segments. For example, in subject S2 with moderate SDB, the mean delta-frequency power was higher than average during early expiration and late inspiration, and lower than average during early inspiration (p=0.0001, FIG. 5A). A similar pattern was generally observed in the other subjects, and for each of the three EEG frequency bands.

Pre-operative alpha RCREC predicted pre-operative sleepiness (mean sleep latency on the MSLT), whereas rates of apneic events did not. The pre-operative apnea/hypopnea index (AHI) showed significant associations with delta and theta RCREC, but not alpha RCREC as shown in the table below:

|  | Delta RCREC | Theta RCREC | Alpha RCREC | MSL | IVA |
| --- | --- | --- | --- | --- | --- |
| AHI | 0.65 (0.0425) | 0.87 (0.0012) | 0.30 (0.4047) | −0.08 (0.8287) | −0.04 (0.9203) |
| MSL | −0.24 (0.5109) | 0.12 (0.7514) | −0.70 (0.0251) | | |
| IVA | −0.15 (0.6876) | −0.05 (0.8939) | 0.06 (0.8675) | | |

In contrast, alpha RCREC correlated with the mean sleep latency on the MSLT, whereas the apnea/hypopnea index, delta RCREC, and theta RCREC did not. No polysomnographic variable correlated significantly with the IVA measure of auditory attention.

Figure 6:
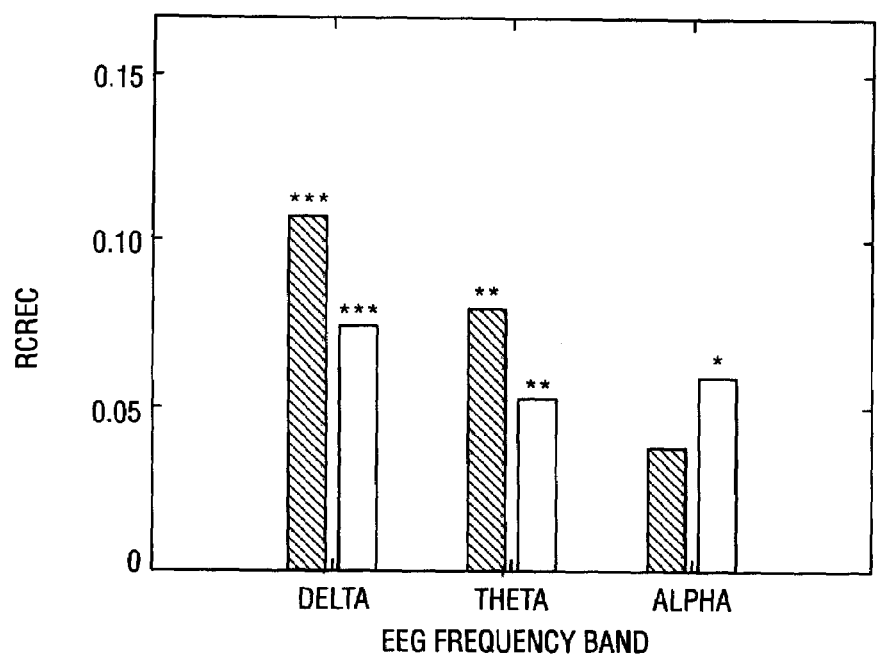
FIG. 6 is a graph of RCREC within delta, theta, and alpha EEG frequency bands for the subject of FIG. 5, wherein the black bars are prior to adenotonsillectomy and the white bars are after adenotonsillectomy.

The tendency of delta-frequency power to vary with the respiratory cycle was diminished after surgery in subject S2 (FIG. 5B), as it was in 4 of 5 subjects with pre-operative obstructive sleep apnea and 2 of 5 subjects without demonstrable obstructive sleep apnea. In FIG. 6, the magnitudes of delta-frequency RCREC was calculated as the differences between the most positive and negative bars exemplified in FIG. 5, and an analogous approach generated values for RCREC in theta and alpha frequency ranges. For subject S2, the magnitudes of RCREC for delta and theta frequencies were high and statistically significant before surgery (FIG. 6, black bars); after surgery that eliminated obstructive sleep apnea, RCREC were lower for delta and theta frequencies but higher for alpha frequencies (FIG. 6, white bars; *$p<0.01$, $p<0.001$, *$p<0.0001$ for the within-subject comparisons of respiratory cycle segment-specific EEG powers by ANOVA under the assumption that these powers follow an F-distribution).

After surgery, the decrement in the apnea/hypopnea index was correlated with the decrement in theta RCREC and showed a trend toward correlation with the decrement in delta RCREC, as shown in the following table:

purposefully selected because of prominent RCREC, suggests that the distribution of results generated by the system and method of the present invention does not always follow a perfect F-distribution.

The above study shows that EEG power in the specific frequency bands which help to define sleep and wakefulness can vary in conjunction with the respiratory cycle. The data suggest that the magnitude of RCREC decreases when SDB is treated, diminishes less after adenotonsillectomy when no SDB was initially detected by standard measures, and gives appropriately mixed results when more subtle SDB is present both pre- and post-intervention. Subjects with clear polysomnographic evidence of SDB all showed statistically significant delta or theta RCREC. The RCREC in delta and theta ranges improved after surgical treatment for SDB. These analyses suggest that delta and theta RCREC vary together with the apnea/hypopnea index. Alpha RCREC may predict at least one important outcome of SDB—objectively-measured daytime sleepiness—better than does the apnea/hypopnea index. After treatment of SDB, the decrement in delta RCREC shows promise, in comparison to the decrement in apnea/hypopnea index, as a better predictor of decreased sleepiness and inattention.

Within respiratory cycles, the alpha RCREC generally varied with, rather than opposite to, the delta RCREC. This result does not make sense if delta activity is a marker for deeper non-REM sleep and alpha activity is a marker for

|  | Delta RCREC | Theta RCREC | Alpha RCREC | MSL | IVA |
| --- | --- | --- | --- | --- | --- |
| AHI | 0.62 (0.0558) | 0.83 (0.0032) | 0.17 (0.6383) | −0.24 (0.4984) | −0.07 (0.8408) |
| MSL | −0.75 (0.0133) | −0.52 (0.1276) | −0.31 (0.3848) |  |  |
| IVA | −0.31 (0.3833) | 0.01 (0.9867) | 0.15 (0.6751) |  |  |

Figure 7:
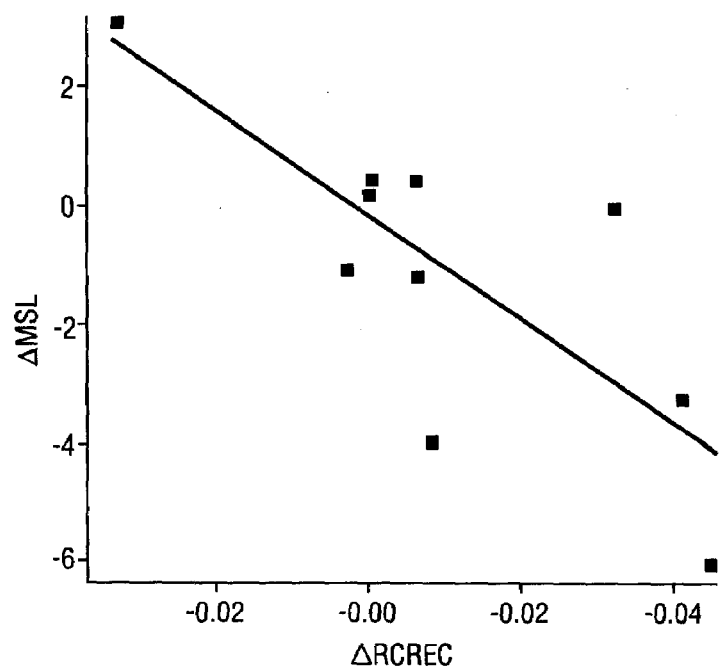
FIG. 7 is a graph of the change in sleepiness one year after surgery as predicted by the change in delta frequency RCREC, wherein MSL is the mean sleep latency in minutes on the Multiple Sleep Latency Test.

After surgery, the change in delta RCREC—but not the change in the apnea/hypopnea index—predicted the change in sleepiness scores (FIG. 7; regression was $\Delta MSL=-0.16 -87.489(\Delta RCREC)$ with $F=11.95$, $p=0.009$, and $R^2=0.60$). In addition, the delta RCREC showed promise, compared to the apnea/hypopnea index, as a predictor of improved attention. The change in theta RCREC also had predictive value.

To confirm that the detection of RCREC was not dependent on long periods of data that include about 2000 respiratory cycles, and also not a byproduct of hypopneas, a shorter segment of 101 consecutive respiratory cycles was identified from the pre-operative study of another subject. Visual inspection of this portion of the recording revealed no apneic events, but delta RCREC remained highly significant ($p=0.001$).

Two types of control analyses also were performed to check whether RCREC might be an artifact. First, the EEG signal from one child was compared to the airflow signal of another child, and adjustment was made for any potential correlation between the airflow of the two subjects. This analysis also showed no significant RCREC. Second, a random noise signal (zero-mean, unit variance Gaussian) was used, instead of the EEG signal from S2, for comparison to S2's pre-operative respiratory cycle segments. A randomly varied start-point within the noise signal was used to produce 1000 iterations of this analysis. For delta RCREC, 107 iterations showed ANOVA results with $p<0.05$; for theta RCREC, 104 iterations; for alpha RCREC, 80 iterations. The number of positive samples that would have been expected in each case is 50. This control analysis, in a subject arousal. However, recent data suggest that alpha activity recorded over frontal cortex, which could contribute to signals at central leads, does correlate with frontal delta activity (see Ferrara et al., *Neuroscience Research* 2002, 44:83–9). Furthermore, the present observation with RCREC would not be the first instance in which alpha and delta activity are noted to occur together in pathological conditions: "alpha-delta" sleep is a well-described feature of fibromyalgia and other conditions that involve chronic pain (see Moldofsky et al., *Psychosomatic Medicine* 2002, 37:341–51). Another explanation for parallel changes in delta and alpha EEG power in the present data could be that RCREC arises not because of arousal but because the brain moves slightly farther from the skull with each inspiration and slightly closer with expiration. Such movement might be enhanced by partial obstruction of the airway, which would increase fluctuation of intrathoracic pressures that could, in turn, be transmitted into the cranium where they could influence EEG power in synchrony with respiration.

The early portion of the night analyzed herein is most likely to demonstrate high amounts of slow wave sleep, essential for the recuperative function of sleep (see Dijk et al., *Am J Physiol* 1990, 258:R650–61), and therefore most likely to show respiratory cycle-related changes that could affect daytime sleepiness. However, other portions of the night or analyses within specific sleep stages could show different results.

An additional study explored whether RCREC on a single pre-operative polysomnogram may predict improvement in behavior or sleepiness one year after surgery. Subjects were 34 children, 19 boys and 15 girls, aged 5.5 to 12.5 years at study entry. Nocturnal polysomnography and neurobehavioral evaluations were performed before and after adenotonsillectomy that had been scheduled for any clinical indication. Obstructive sleep apnea was defined by a pediatric (2-breath, thermocouple derived) obstructive apnea index >0.5. Pre-operative RCREC obtained using the STFT technique were tested for correlation with post-operative changes in hyperactivity and sleepiness. Inattentive and hyperactive behavior was assessed by a behavioral index, the average of T-scores from two well-validated parent-rating instruments. Sleepiness was assessed by MSLT.

Pre-operative delta-range RCREC predicted improvement in behavior (Spearman rho=0.36, p=0.04) whereas the apnea/hypopnea index and the visually-scored arousal index did not (rho=−0.30, p=0.09; rho=−0.21, p=0.24). In the subgroup of 16 children with obstructive sleep apnea, as defined by an obstructive apnea index of 1 or more event per hour, the association between baseline RCREC and improvement in the behavioral index was stronger (rho=0.68, p=0.004), whereas the apnea/hypopnea and arousal indices again were not predictive (rho=−0.04, p=0.88; rho=0.18, p=0.50). Similarly, among the 34 adenotonsillectomy subjects, improvement in sleepiness on the MSLT was predicted by initial delta RCREC (rho=−0.41, p=0.015), but not by apnea/hypopnea or arousal indices (rho=−0.09, p=0.62; rho=−0.03, p=0.88).

In yet another analysis, data on RCREC were generated via digital filtering for a total of 156 sleep studies from 78 children aged 5.3 to 12.5 years. Sixty-six of these children underwent adenotonsillectomy, 31 had significant SDB by the most common pediatric criterion (obstructive apnea index ≧1), and 12 were controls. As described below, these data provide information on the meaning of RCREC, its relation to standard sleep measures, its behavior before and after treatment for SDB, its covariance with important neurobehavioral outcomes, and its clinical utility, especially in circumstances when standard sleep measures prove unhelpful.

At baseline, delta and alpha RCREC tended to correlate with the standard apnea/hypopnea index, but not strongly (Spearman rho=0.24 and 0.20, respectively; p=0.03 and 0.07). Associations with other traditional measures of SDB severity—such as the EEG arousal index and minimum oxygen saturation—were not significant, but that between delta RCREC and an esophageal pressure measure (percent sleep time spent with esophageal pressure more negative than −10 cm of water) was significant (rho=0.32, p=0.02). In a multiple stepwise regression model of these 4 SDB measures, only the percent of sleep time spent with high negative pressures (indicative of increased respiratory effort) independently predicted delta RCREC (p=0.006). In an analogous model, no measure predicted alpha RCREC (p>0.05). Therefore, these results indicate that RCREC varies only moderately, if at all, with other SDB measures (known to be suboptimal), and best with the gold-standard measure of respiratory effort (esophageal pressure).

After adenotonsillectomy, delta RCREC diminished from 0.051±0.026 to 0.043±0.022 (paired t-test, p=0.04), and alpha RCREC from 0.058±0.032 to 0.055±0.030 (p=0.4). Among control subjects, the respective changes were from 0.037±0.023 to 0.039±0.023 (p=0.8), and from 0.048±0.017 to 0.047±0.011 (p=1.0). Therefore, in contrast to essentially complete normalization of standard SDB measures after adenotonsillectomy, delta RCREC showed a more moderate decrease and alpha RCREC very little change. Neurobehavioral changes may parallel changes in RCREC more closely than those in standard measures: among 29 adenotonsillectomy subjects with disruptive behavior disorders prior to surgery, 14 no longer qualified for these diagnoses one year later, but 15 still did.

Pre-operative, cross-sectional relationships between sleep variables and neurobehavioral morbidity were tested more directly. ANOVA was used to compare behavioral measures between three groups: A) controls (n=27), B) "normal" adenotonsillectomy subjects, and C) "abnormal" adenotonsillectomy subjects, with the 66 adenotonsillectomy subjects being divided into groups B and C by either the standard obstructive apnea index ≧1 (n=34) or delta RCREC>0.05 (n=27). These analyses consistently showed that neurobehavioral morbidity was worse in adenotonsillectomy subjects than controls, but highly similar in the two adenotonsillectomy groups defined by the apnea index. For example, the Child Symptom Inventory-4 (CSI-4) ADHD T score was 13.0 points higher in high-apnea subjects than in controls, but also 13.4 points higher in low-apnea subjects than in controls (post-hoc Bonferroni t-test for high vs. low-apnea groups, p>0.05). Disruptive behavior disorders were diagnosed in 38% of high-apnea subjects, 40% of low-apnea subjects, and 11% of controls. In contrast, the same CSI-4 ADHD T score was 23.6 points higher in high-RCREC subjects than in controls, and only 8.7 points higher in low-RCREC subjects than in controls (high vs. low-RCREC groups p<0.05). Disruptive behavior disorders were diagnosed in 52% of the adenotonsillectomy subjects with high RCREC, 31% of those with low RCREC, and 11% of controls (chi-square p 0.005). Differences between performance of standard measures and RCREC were also demonstrated by nonparametric Spearman correlations with other attention and achievement measures. For example, among all subjects, delta RCREC, alpha RCREC, or both tended to correlate inversely with the CMS attention/concentration scale (p<0.05), WIAT mathematical reasoning (p<0.10), and WIAT reading comprehension (p<0.05). In contrast, standard measures—including the apnea/hypopnea index, EEG arousal index, and minimum oxygen saturation—failed to show any trend toward correlation with these outcomes (all p>0.10). Sleepiness and IQ did not correlate with any polysomnographic measure. Overall, then, these results demonstrate that the most common criterion used to identify pediatric SDB does not distinguish between adenotonsillectomy patients with and without neurobehavioral morbidity, whereas the RCREC measure according to the present invention generally does.

If the RCREC are sensitive to some aspect of SDB linked to neurobehavioral consequences, then this new measure could have important clinical utility, particularly when behavior is a concern but standard sleep measures are normal as occurs with some frequency prior to potential adenotonsillectomy or after the surgery. Prior to adenotonsillectomy or control procedures, among 47 subjects with an apnea index <1, delta RCREC tended to correlate with the CMS attention/concentration score (rho=−0.28, p=0.06) and the WIAT-mathematical reasoning score (rho=−0.31, p=0.03). Alpha RCREC tended to correlate with these scores (rho=−0.24, p=0.10; rho=−0.31, p =0.04 respectively) and with the CSI-4 ADHD T score (rho=0.33, p=0.02), full-scale IQ (rho=−0.36, p=0.01), and WIAT reading comprehension (rho=−0.34, p=0.03). In contrast, the apnea/hypopnea index, EEG arousal index, and minimum oxygen saturation showed no trend toward association with any of these variables. When sleep and neurobehavioral testing was repeated one year after surgery in 78 subjects, delta RCREC correlated with scores on objective tests of sleepiness and attention (both p<0.05). In contrast, no standard sleep variable did so. Therefore, the RCREC measure of the present invention appears to be useful in common clinical settings in which behavioral issues can still be a concern but standard polysomnographic measures generally show normal results.

Polysomnography prior to adenotonsillectomy would be most useful if it could predict which children are likely to experience long-term neurobehavioral improvement after the procedure. Among the tested subjects, no standard polysomnographic measure at baseline predicted post surgical change in sleepiness, hyperactivity ratings, IQ, attention/concentration, or achievement (all p>0.05). In contrast, pre-operative RCREC performed better. For example, delta RCREC predicted reduction in sleepiness (rho=−0.26, p=0.02), and alpha RCREC predicted improvement in full-scale IQ (rho=−0.23, p=0.05) and achievement (WIAT reading comprehension rho=−0.24, p=0.05). Some such associations were stronger in the subgroup of adenotonsillectomy children who originally had SDB (obstructive apnea index >1), whereas others were stronger among those without SDB. For example, among adenotonsillectomy subjects with SDB, both delta and alpha RCREC predicted improvement in IQ (rho =−0.38, p=0.04; rho=−0.43, p=0.02 respectively). Among those without SDB, alpha RCREC still predicted improvement in reading comprehension (rho=−0.42, p=0.005). Among adenotonsillectomy subjects with pre-operative SDB by a standard measure (obstructive apnea index $\geq 1$), 15% no longer had attention-deficit/hyperactivity disorder one year later, but neither did 14% of those without SDB. In contrast, among adenotonsillectomy subjects with high pre-operative delta RCREC (>0.05), 22% no longer had attention-deficit/hyperactivity disorder one year after surgery; among subjects with low pre-operative RCREC, only 10% achieved the same benefit (Fisher's exact test, p>0.05). Therefore, the RCREC measures are likely to enhance the clinical value of polysomnography performed prior to adenotonsillectomy, especially when SDB is present but sometimes even when standard measures reveal no SDB.

These results demonstrate that the RCREC measure according to the system and method of the present invention appears to measure a previously unsuspected physiological process that links disordered breathing to brain function: transient changes in EEG power occur on a breath-to-breath basis in SDB. Furthermore, RCREC predicts measured levels of sleepiness, cognitive, and behavioral morbidity substantially better than do traditional, gold-standard measures of SDB severity. The magnitude of RCREC appears to reflect the severity of SDB, and RCREC diminishes robustly after successful treatment for SDB. Demonstration of RCREC and the findings of the above studies have potentially important implications for SDB physiology, neurobehavioral consequences, and clinical practice in both children and adults.

One such implication is that visualized or computer-detected arousals after apneic events are not the only mechanism by which SDB may disrupt cortical function. No prior research has defined a minimum duration that allows arousals, of sufficient frequency, to attain clinical significance. Previous studies that have used autonomic or spectral EEG markers of arousal in SDB focused on a time frame equivalent to several breaths or more (see Black et al., *Am J Resp Crit Care Med* 2000, 162:406–11; Bandla and Gozal, *Pediatr Pulmonol* 2000, 29:359–65; Dingli et al., *Eur Respir J* 2002, 20:1246–53; Rees et al., *Am J Resp Crit Care Med* 1995, 152:1016–21; Svanborg and Guilleminault, *Sleep* 1996, 19:248–54). One study did identify non-specific EEG power variation, between successive 60-second windows, as a significant predictor of sleepiness among patients referred for suspected obstructive sleep apnea (see Bennett et al., *Am J Resp Crit Care Med* 1998, 158:778–86). Another study of severe sleep apneics and controls showed that decreased slow wave activity in the first nocturnal sleep cycle correlates with sleepiness on a Multiple Sleep Latency Test, and that continuous positive airway pressure improves early-night slow wave activity (see Heinzer et al., *Chest* 2001, 119:1807–13). However, no previous method has addressed the possibility that breath-to-breath changes in EEG power—too quick or subtle to have been detected by human eye—could nonetheless have profound influence over the course of the night.

RCREC appears to represent "microarousal" that occurs, on average, with each partially obstructed breath cycle. Increased respiratory effort associated with each breath might cause subtle but repetitive and numerous microarousals. However, other possible explanations for RCREC also exist. This measure could represent a cortical evoked potential triggered by airway obstruction. Of note, noise could also generate arousals, K-complexes, or other evoked potentials, and therefore snoring could conceivably be another cause of RCREC.

As evidence above, RCREC may predict important outcomes of SDB, and thus potential applications are numerous. Standard polysomnographic measures show only limited ability to predict outcomes such as daytime sleepiness and cognitive dysfunction. Lack of obvious apneas and arousals in many children compounds the problem in this age group. Currently standard variables, such as the apnea/hypopnea index, suffer from biological variability between nights and between laboratories with different human scorers, recording equipment, and event definitions. Standard 3-second arousals can be challenging to score reliably. The RCREC system and method of the present invention, which requires only one non-quantitative measure of breathing and one EEG lead, could lead to simple improvements in home monitoring equipment or self-adjusting continuous positive airway pressure machines. The RCREC measure according to the present invention provides an efficient method to assess breathing and cortical function during most of the night rather than the minority spent in a state of apnea or visible arousal, improves prediction of important outcomes, and is simple, reliable, and cost-effective enough for widespread use.

The system and method of the present invention may shed light on how SDB affects the brain. The analytic technology of the present invention could lead to more physiologically and clinically-relevant assessment of SDB, as individuals whose polysomnograms currently show little or no evidence of SDB might receive a diagnosis with this technology. Residual sleepiness, neurobehavioral problems, or psychiatric disorders are common after treatment for SDB; the reason is often unclear after standard sleep laboratory assessments, but might be clarified by the system and method of the present invention.

In comparison to technology previously available, the present invention provides a more accurate, clinically informative, and physiologically relevant measure of SDB. The invention will enhance the value of data collected during sleep studies, at comparatively little added cost. Adoption of the RCREC new measure according to the present invention could help to automate sleep laboratory record processing, improve test-retest reliability, reduce large inter-laboratory disparities that arise from human scoring, and lower costs for technical time and expertise. Software according to the present invention might be used to provide online feedback to optimize manual or automated titration of nasal continuous positive airway pressure, the main treatment for adult SDB. In addition to clinicians, researchers can use the system and method of the present invention to investigate whether RCREC shows associations between sleep-disordered breathing and many suspected but unproven outcomes, including hypertension, stroke, coronary artery disease, myocardial infarction, heart failure, arrhythmias, cognitive dysfunction, and increased mortality.

Treatment of obstructive SDB is most often accomplished by use of a mechanical device called continuous positive airway pressure, or CPAP. The CPAP machines are usually set to a pressure setting determined to be effective during all parts of a night spent, at significant expense, in a sleep laboratory. Recently, CPAP manufacturers have produced machines that use various proprietary algorithms to determine the required pressure—which in reality varies constantly—all through the night, every night, at home. These continuously self-adjusting CPAP units have gained some popularity, and would be much more popular they could more effectively determine optimal pressure levels. The present invention could be incorporated into self-adjusting CPAP machines to make them responsive to what may be the most physiologically important aspects of poorly controlled SDB.

The present invention could also substantially improve home diagnostic recording devices. As most patients with sleep apnea are undiagnosed, and current sleep laboratory facilities are not nearly sufficient to diagnose all affected patients in a timely manner, considerable industry and entrepreneurial effort is now expended to devise simpler, less costly, ambulatory recording systems. Although many such systems have been manufactured during the past 2 decades, none has gained widespread popularity, in part because accuracy in comparison to laboratory studies is often lacking. The present invention could be adapted easily to home monitoring systems, and could allow these systems to identify pathology relevant to outcomes in a manner that would exceed current laboratory-based capabilities.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for determining respiratory cycle-related EEG changes (RCREC) for a subject, the method comprising:
   receiving an EEG signal from the subject using at least one EEG sensor;
   defining at least two respiratory cycle segments within each respiratory cycle;
   determining an EEG power of the EEG signal during each of the at least two respiratory cycle segments; and
   determining RCREC by calculating a difference between a maximum EEG segment power and a minimum EEG segment power.

2. The method according to claim 1, wherein determining an EEG power includes digitally filtering the EEG signal.

3. The method according to claim 2, wherein digitally filtering the EEG signal utilizes at least one $5^{th}$ order Butterworth filter.

4. The method according to claim 1, wherein determining the EEG power includes taking a short-time Fourier transform of the EEG signal.

5. The method according to claim 1, wherein determining an EEG power includes determining the EEG power for one or more frequencies within at least one of a delta (approximately 1–4 Hz) frequency range, a theta (approximately 5–7 Hz) frequency range, an alpha (approximately 8–12 Hz) frequency range, a sigma (approximately 13–15 Hz) frequency range, and a beta (approximately 16–30 Hz) frequency range.

6. The method according to claim 1, further comprising normalizing the EEG power for each respiratory cycle segment by a mean EEG power during the entire respiratory cycle.

7. The method according to claim 1, further comprising averaging the EEG segment powers over a plurality of respiratory cycles.

8. The method according to claim 1, further comprising receiving a respiratory signal from the subject.

9. The method according to claim 8, wherein the respiratory signal includes at least one of a nasal airflow and an oral airflow.

10. The method according to claim 1, wherein the respiratory signal includes at least one of a chest excursion and an abdominal excursion.

11. The method according to claim 1, wherein the respiratory signal includes an intrathoracic pressure.

12. The method according to claim 1, wherein the respiratory signal includes respiratory muscle activity.

13. The method according to claim 1, wherein the at least two respiratory segments include four fixed time segments defined by maxima, minima, and midpoints of inspiratory and expiratory phases of the respiratory cycle.

14. The method according to claim 1, wherein receiving the EEG signal includes recording the signal over about the first three hours of nocturnal sleep.

15. The method according to claim 1, further comprising amplifying the EEG signal.

16. The method according to claim 1, further comprising converting the EEG signal from analog to digital format.

17. The method according to claim 1, further comprising storing EEG data in memory.

18. The method according to claim 1, further comprising displaying EEG data on a display.

19. The method according to claim 1, further comprising comparing values of RCREC before and after intervention to treat sleep-disordered breathing.

20. The method according to claim 1, further comprising comparing RCREC values with values of a sleepiness measure.

21. A method for analyzing respiratory cycle related EEG changes (RCREC) in a subject with sleep-disordered breathing, the method comprising:
   receiving an EEG signal from the subject using at least one sensor;
   receiving a respiratory signal to define at least two respiratory cycle segments within each respiratory cycle;
   determining an EEG power of the EEG signal for each of the respiratory cycle segments within at least one frequency range;
   normalizing the EEG power for each respiratory cycle segment by a mean EEG power during the entire respiratory cycle;
   averaging the normalized EEG segment powers over a plurality of respiratory cycles; and
   determining RCREC by calculating a difference between a maximum EEG segment power and a minimum EEG segment power.

22. A system for determining respiratory cycle-related EEG changes (RCREC) in a subject, the system comprising:
   at least one EEG sensor arranged obtain an EEG signal from the subject;
   a respiratory measurement device for defining at least two segments of each respiratory cycle;
   a processor in communication with the at least one sensor and the respiratory measurement device, the processor determining an EEG power of the EEG signal for each of the at least two respiratory cycle segments, and determining RCREC by calculating a difference between a maximum EEG segment power and a minimum EEG segment power.

23. The system according to claim 22, wherein the processor utilizes digital filtering of the EEG signal to determine the EEG power.

24. The system according to claim 23, wherein the processor utilizes at least one $5^{th}$ order Butterworth filter.

25. The system according to claim 22, wherein the processor utilizes a short-time Fourier transform of the EEG signal to determine the EEG power.

26. The system according to claim 22, wherein the processor determines the EEG power for one or more frequencies within at least one of a delta (approximately 1–4 Hz) frequency range, a theta (approximately 5–7 Hz) frequency range, an alpha (approximately 8–12 Hz) frequency range, a sigma (approximately 13–15 Hz) frequency range, and a beta (approximately 16–30 Hz) frequency range.

27. The system according to claim 22, wherein the processor normalizes the EEG power for each respiratory cycle segment by a mean EEG power during the entire respiratory cycle.

28. The system according to claim 22, wherein the processor averages the EEG segment powers over a plurality of respiratory cycles.

29. The system according to claim 22, wherein the respiratory measurement device includes at least one airflow sensor for measuring at least one of a nasal airflow and an oral airflow.

30. The system according to claim 29, wherein the at least one airflow sensor includes a thermocouple.

31. The system according to claim 22, wherein the respiratory measurement device includes at least one position sensor for measuring at least one of a chest excursion and an abdominal excursion.

32. The system according to claim 22, wherein the respiratory measurement device includes at least one pressure sensor for measuring intrathoracic pressure.

33. The system according to claim 22, wherein the respiratory measurement device includes at least one EMG sensor for measuring respiratory muscle activity.

34. The system according to claim 22, further comprising an amplifier in communication with the at least one EEG sensor for amplifying the EEG signal.

35. The system according to claim 22, further comprising an A/D converter in communication with the processor for converting the EEG signal from analog to digital format.

36. The system according to claim 22, further comprising memory in communication with the processor for storing EEG data.

37. The system according to claim 22, further comprising a display in communication with the processor for displaying EEG data.

38. A computer readable medium for determining respiratory cycle-related EEG changes (RCREC) in a subject, the medium comprising:
   computer readable instructions for determining an EEG power of a received EEG signal for a plurality of respiratory cycle segments, and determining RCREC by calculating a difference between a maximum EEG segment power and a minimum EEG segment power.

39. The medium according to claim 38, further comprising computer readable instructions for normalizing the EEG power for each respiratory cycle segment by a mean EEG power during the entire respiratory cycle.

40. The medium according to claim 38, further comprising computer readable instructions for averaging the normalized EEG segment powers over a plurality of respiratory cycles.

* * * * *